(12) United States Patent  
Schwotzer

(10) Patent No.: US 7,522,764 B2  
(45) Date of Patent: Apr. 21, 2009

(54) METHOD AND SYSTEM FOR IMAGING AN OBJECT

(75) Inventor: Axel Schwotzer, Gross-Gerau (DE)

(73) Assignee: Sirona Dental Systems GmbH, Bensheim (DE)

( * ) Notice: Subject to any disclaimer, the term of this patent is extended or adjusted under 35 U.S.C. 154(b) by 822 days.

(21) Appl. No.: 10/757,507

(22) Filed: Jan. 15, 2004

(65) Prior Publication Data

US 2004/0151369 A1 Aug. 5, 2004

(30) Foreign Application Priority Data

Jan. 31, 2003 (DE) .................... 103 04 111

(51) Int. Cl.
- *G06K 9/00* (2006.01)
- *G06K 9/40* (2006.01)
- *G06K 9/36* (2006.01)
- *G01B 11/24* (2006.01)
- *A61C 3/00* (2006.01)

(52) U.S. Cl. .............. 382/154; 382/108; 382/254; 382/284; 356/601; 433/24; 433/196

(58) Field of Classification Search ............ 382/108, 382/106, 154, 254–277, 284–285; 433/24, 433/196; 356/2–22, 601–636
See application file for complete search history.

(56) References Cited

U.S. PATENT DOCUMENTS

| | | | |
|---|---|---|---|
| 3,879,133 A * | 4/1975 | Mathieu ................. | 356/394 |
| 4,212,073 A * | 7/1980 | Balasubramanian ...... | 702/167 |
| 4,818,110 A * | 4/1989 | Davidson ............... | 356/512 |
| 4,837,732 A * | 6/1989 | Brandestini et al. ...... | 433/29 |
| 4,929,951 A * | 5/1990 | Small .................. | 342/179 |
| 4,971,435 A * | 11/1990 | Shaw et al. ............ | 352/59 |

(Continued)

OTHER PUBLICATIONS

Peisen S. Huang, Qingying Hu, Feng Jin and Fu-Pen Chiang, "Color-encoded fringe projection and phase shifting for 3-D surface contouring", 1998, SPIE, vol. 3407, pp. 477-482.*

(Continued)

*Primary Examiner*—Matthew C Bella  
*Assistant Examiner*—Manav Seth  
(74) *Attorney, Agent, or Firm*—Dykema Gossett PLLC

(57) ABSTRACT

In a method of imaging an object, for dental purposes, comprises:

a) projecting a striped pattern on to the object to be imaged, b) recording the projected striped pattern as a basic image ($R_i$) with a camera, steps a) and b) being carried out at a number of different positions of the phase relationship of the striped pattern, and c) computing an image of the object from the plurality of mutually out-of-phrase basic camera images. Provision is made for suppression of periodic disturbances in that, in step c), $c_1$) at least two groups of basic images ($R_1, R_2, \ldots, R_n$; $R_2, R_3, \ldots, R_{n+1}$) are formed from the basic camera images ($R_1, \ldots, R_m$), $c_2$) a phase related image (Pj) of the object to be imaged (20) is computed from each group of basic images ($R_1, R_2, \ldots, R_n$; $R_2, R_3, \ldots, R_{n+1}$), $c_3$) the computed phase related images ($P_1, P_2$) are averaged such that a phase related image (P) having a reduced amount of noise is formed, and that $c_4$) an image of the object is computed from the phase related image (P) having a reduced amount of noise.

37 Claims, 3 Drawing Sheets

U.S. PATENT DOCUMENTS

| | | | | |
|---|---|---|---|---|
| 5,471,307 A | * | 11/1995 | Koliopoulos et al. | 356/613 |
| 5,509,090 A | * | 4/1996 | Maruyama et al. | 382/276 |
| 5,555,090 A | * | 9/1996 | Schmutz | 356/601 |
| 5,867,604 A | * | 2/1999 | Ben-Levy et al. | 382/254 |
| 5,912,557 A | * | 6/1999 | Wilman et al. | 324/309 |
| 6,175,411 B1 | * | 1/2001 | Telschow et al. | 356/503 |
| 6,229,913 B1 | * | 5/2001 | Nayar et al. | 382/154 |
| 6,249,616 B1 | * | 6/2001 | Hashimoto | 382/284 |
| 6,438,272 B1 | * | 8/2002 | Huang et al. | 382/286 |
| 6,648,640 B2 | * | 11/2003 | Rubbert et al. | 433/24 |
| 6,775,403 B1 | * | 8/2004 | Ban et al. | 382/154 |
| 6,813,377 B1 | * | 11/2004 | Gopalakrishnan et al. | 382/146 |
| 6,853,458 B2 | * | 2/2005 | Yahashi et al. | 356/604 |
| 6,985,175 B2 | * | 1/2006 | Iwai et al. | 348/187 |
| 7,068,376 B2 | * | 6/2006 | De Groot | 356/497 |
| 7,149,337 B2 | * | 12/2006 | Michaelis et al. | 382/141 |
| 7,310,154 B2 | * | 12/2007 | Kitaguchi et al. | 356/603 |
| 2003/0026475 A1 | * | 2/2003 | Yahashi et al. | 382/154 |
| 2008/0279446 A1 | * | 11/2008 | Hassebrook et al. | 382/154 |

OTHER PUBLICATIONS

C. Joenathan, "Phase-measuring interferometry: new methods and error analysis", 1994, Optical Society of America, vol. 33, No. 19, pp. 4147-4155.*

A. H. Wilcock and R. L. G. Kirsner, "A Digital Filter for Biological Data", 1969, Pergamon Press, Med. & biol. Engng., vol. 7, pp. 653-660.*

Robert Windecker and H. J. Tiziani, "Semispatial, robust, and accurate phase evaluation algorithm", 1995, Optical Society of America, vol. 34, No. 1, pp. 7321-7326.*

* cited by examiner

METHOD AND SYSTEM FOR IMAGING AN OBJECT

TECHNICAL FIELD

The invention relates to a method of creating an image of an object, particularly for dental purposes, comprising the following method steps: a) projecting a striped pattern on to the object to be imaged, b) recording the projected striped pattern as a basic image with a camera, the steps a) and b) being carried out at a number of different positions of the phase relationship of the striped pattern, and c) computing an image of the object to be imaged from the plurality of mutually out-of-phase basic camera images. Suitable images are, in particular, relief images or contrast images.

BACKGROUND OF THE INVENTION

Direct optical three-dimensional surveying of one or more teeth in the mouth of a patient can provide digital construction data for the computer-controlled production of dentures without using a dental impression. Such a three-dimensional representation, known as an "optical impression" in analogy to physical molding, can be made with one or more camera images without contacting the object. The camera can be freely guided for this operation like an angled handpiece or guided with one or both hands whilst supported on the teeth.

The method of measurement implements the principle of active triangulation, in which a single stripe of light or a striped pattern of parallel stripes of light is projected on to the object to be imaged by projecting means and the projected image is recorded by a two-dimensional camera at an angle of parallax.

By reason of the surface texture of the teeth the projected stripe is no longer a straight line but appears to be curved and displaced relatively to the straight path. The position of the lines of light can provide information on the surface texture of the object being imaged. Following the measuring procedure, the memory of the computer contains a digital three-dimensional data model of the imaged object, which can be displayed, for example, on a monitor as a still video picture or can serve as the basis for the computer-controlled production of a denture.

In order to increase accuracy, use may be made of the phase-shifting triangulation method. This method involves the successive production of a number of basic images at various positions of the phase relationship of the grid, and from these images a phase related image is computed. From the phase related image it is then possible, with the aid of calibration data, to compute a relief image of the object. Various algorithms for the computation of the phase related image from the individual basic images are known. For example, three, four, or five basic images showing a relative phase shift of 120° or 90° can be recorded. It is also possible to compute a contrast image from the basic images. For example, a contrast image can be computed from four basic images having intensities $I_1 \ldots I_4$ according to the formula:

$$K = \sqrt{((I_1 - I_3)^2 + (I_2 - I_4)^2)}.$$

The phase-shifting method involves, on account of tolerances or systematic sources of error, typical periodic disturbances or noise. These periodic disturbances occur in the phase related image and also in the contrast image or relief image at a multiple of the grid frequency.

For example, any deviation from the linear motion of the optical grid leads to noise at 2-fold grid frequency, any change in the intensity of the grid illumination to noise at 1-fold grid frequency, and deviations from the linearity between the light signal and electrical signal leads to noise at 4-fold grid frequency.

In general, the computing algorithms become less prone to noise generation as the number of recorded basic images increases. Nevertheless, the described periodic disturbances are expressed to various degrees despite the distinctly more elaborate treatment.

The quality of the phase related image and contrast image may be increased, for example, by effecting filtration. This must mean a loss of resolution however. Improvement in quality caused by averaging a plurality of, phase related images or contrast images suffers on the other hand from the drawback of a distinctly prolonged recording time.

It is further possible to effect control over the recording of the basic images in a very precise manner such that the periodic disturbances occur to a lesser extent. However, such precise control involves elaborate means. In addition, external conditions, such as temperature, moisture, or the force of gravity, and also long-term effects have an influence on the imaging process and the image quality obtained.

These problems are solved by the present invention. It is an object of the invention, as characterized in the claims, to provide a method of the above type for creating an image of a an object, which method affords much greater measuring accuracy than known techniques whilst involving comparatively little elaboration.

SUMMARY OF THE INVENTION

The invention improves on the prior art in that suppression of periodic disturbances in the method step c) involving the computation of an image of the object from the plurality of basic camera images that are out-of-phase relatively to each other is effected by:

$c_1$) forming at least two groups of basic images from the basic camera images, $c_2$) computing a phase related image of the object to be imaged from each group of basic images, $c_3$) averaging the computed phase related images using weighting factors, in order to obtain a phase related image having a reduced amount of noise, and $c_4$) computing an image of the object from the phase related image having a reduced amount of noise.

The use of the method $c_1$) to $c_4$) makes it possible to suppress noise in a relief image or in a contrast image. Thus the invention is based on the principle of dividing the basic images into two or more groups such that the noise in the phase related images computed from the respective groups of basic images show a certain degree of phase shift relatively to each other. These phase related images are suitably averaged so as to suppress or eliminate noise of specific multiples of the grid frequency. By this means additional basic imaging can increase the measuring accuracy to a marked degree with only slight prolongation of the total imaging time.

Preferably each of the basic images is recorded in the method of the invention with a constant shift of the phase relationship in the grid.

In a preferred embodiment of the process of the invention, provision is made for recording of (n+1) basic images $R_1, R_2, \ldots, R_{n+1}$, of which successive basic images exhibit a predetermined phase shift. Two groups of basic images $R_1, R_2, \ldots, R_n; R_2, R_3, \ldots, R_{n+1}$ are formed, and a first phase related image $P_1$ is computed from the first group of basic images $R_1, R_2, \ldots, R_n$ and a second phase related image $P_2$ is computed from the second group of basic images $R_2, R_3, \ldots, R_{n+1}$. The first and second phase related images, $P_1$ and $P_2$, are averaged with identical weighting, in order to obtain a phase related image P having a reduced amount of noise. In this case, n is an integer greater than or equal to 3, to make it possible to produce a phase related image by known methods.

Another preferred embodiment of the process of the invention, makes provision for recording of (n+2) basic images $R_1$, $R_2, \ldots, R_{n+2}$, of which each successive basic image exhibits a predetermined phase shift. Three groups of basic images $R_1$, $R_2, \ldots, R_n$; $R_2, R_3, \ldots, R_{n+1}$; $R_3, R_4, \ldots, R_{n+2}$ are formed, and a first phase related image $P_1$ is computed from the first group of basic images $R_1, R_2, \ldots, R_n$, a second phase related image $P_2$ from the second group of basic images $R_2, R_3, \ldots, R_{n+1}$, and a third phase related image $P_3$ from the third group of basic images $R_3, R_4, \ldots, R_{n+2}$. The first and third phase related images $P_1$ and $P_3$ are averaged with identical weighting, in order to obtain an intermediate image $P_z$, and the second phase related image $P_2$ and the intermediate image P are averaged, in order to obtain a phase related image P having a reduced amount of noise. Here n is an integer greater than or equal to 3.

In the case of the two embodiments described above it is preferred that n be equal to 4, because in this case the measuring accuracy and the measurement time required bear a particularly favorable relationship to each other.

According to a development of the method of invention, provision is made for recording the basic images by the interlacing method so that when the striped pattern is continuously moved, the two fields show a phase shift relatively to each other which is half the phase shift between successive basic images. In the interlacing method, the image to be produced is split up into two fields. The first field usually corresponds to the even-numbered lines and the second field to the odd-numbered lines. The two fields are recorded successively and consequently at different times. It is an advantage in this context when a phase related image is computed from each of the fields of a basic image, and the two phase related images are averaged prior to further processing, in order to obtain a phase related image having a reduced amount of high-frequency noise. If, for example, the basic images are recorded with a phase shift of 90° with continuous motion of the grid producing the striped pattern, there results a phase shift between the two fields of 45. Decisive in this case is the time center of the integration phase during the production of the fields, the duration of the integration phase itself, i.e., the duration of exposure of the detector, being of minor importance. In this way, averaging the two phase related images or contrast images can suppress noise having 4 times the grid frequency. This must be coupled with a loss of resolution, but in the case of severe noise the positive effect of noise suppression predominates. Averaging is preferably carried out using a running mean.

Advantageously, one method of the invention is characterized in that, prior to step a), an image of a specific test object is recorded, and, on the basis of an analysis of the image of the test object, a suitable scheme for use in computation of the noise-reduced phase related image for the object to be imaged is selected. Since periodic disturbances governed by external influences can occur either sporadically or may always be present due to the system used, this measure can ensure that an algorithm that prolongs the recording time can only be used when the relevant disturbance occurs during recording.

Recording of the test object can take place without substantial loss of time during the calibration of the system, which is in any case necessary for computation of contrast or relief images from the phase related images. However, it may be also carried out separately, if desired, so that prior to each measurement of an object to be imaged the most favorable computation scheme can be selected.

The method of the invention is of particular advantage for those systems in which the object to be imaged and the camera can be freely positioned relatively to each other for the purpose of recording the projected striped pattern, and free-hand recording can be carried out.

A particularly preferred application example comprises recording a relief image of one or more teeth in the oral cavity of a patient, which is executed over a short measuring period by manual surveying. And the resulting increase in measuring accuracy attained according to the invention without substantial prolongation of the recording time is of special advantage.

A device of the invention for the execution of the aforementioned method comprises projecting means for projecting a striped pattern on to the object to be imaged, a camera for recording the projected striped pattern as a basic image, and means for computing an image of the object to be imaged from a number of basic camera images that are out-of-phase with each other and are grouped to form at least two groups of basic images.

Other advantageous embodiments, features, and details of the invention are revealed in the subclaims, the description of the embodiments, and the drawings.

BRIEF DESCRIPTION OF THE DRAWINGS

The invention is explained in greater detail below with reference to an embodiment in conjunction with the drawings. Only those elements essential for comprehension of the invention are illustrated. In the drawings.

WORKING EXAMPLES

Figure 1:
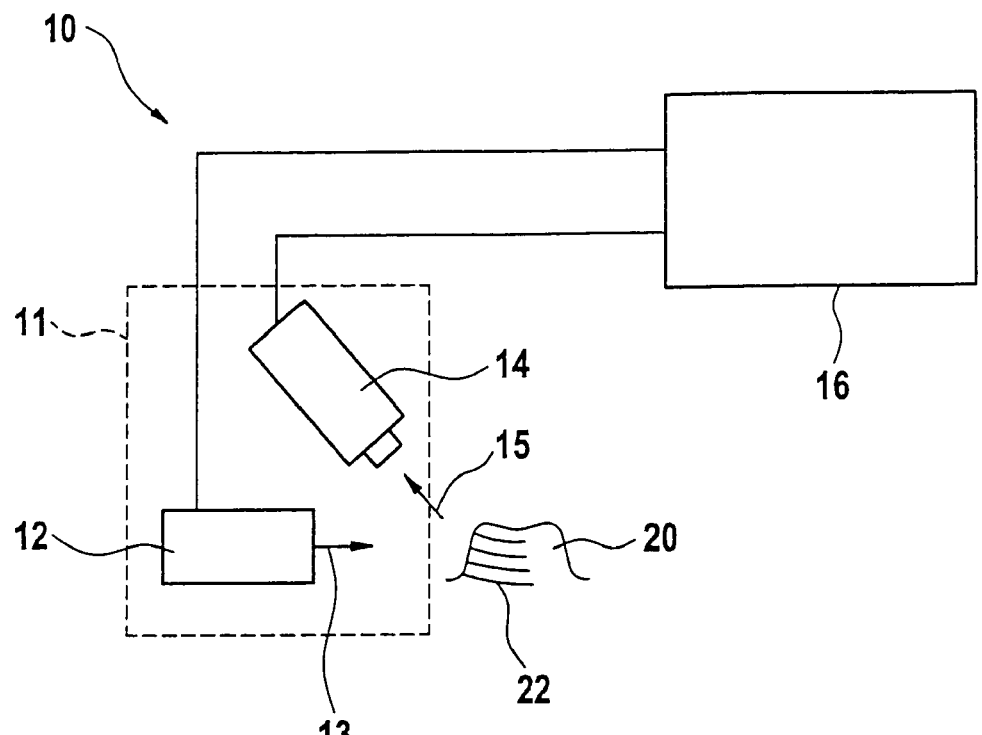
FIG. 1 is a diagrammatic representation of a recording device of the invention conforming to the principle of phase shift triangulation.

FIG. 1 is a diagrammatic representation of a recording device designated by the reference numeral 10 and adapted to operate according to the principle of phase shift triangulation. The projecting device 12 produces a grid of light having parallel grid lines projected on to an object to be imaged, in the present example a tooth 20. By reason of the three-dimensional surface texture of the tooth 20, the lines of light in the grid on the tooth appear to be bent and unevenly spaced. The image 22 projected via the projection ray trajectory 13 is recorded (videographed) at an angle of parallax by means of a two-dimensional camera 14 disposed in the trajectory of observation 15 and is passed on to an evaluation unit 16 for evaluation. The projecting device 12 and the camera 14 may be combined to form a structural unit 11, as will be later shown in FIG. 5 in the case of an intraoral camera.

Figure 2:
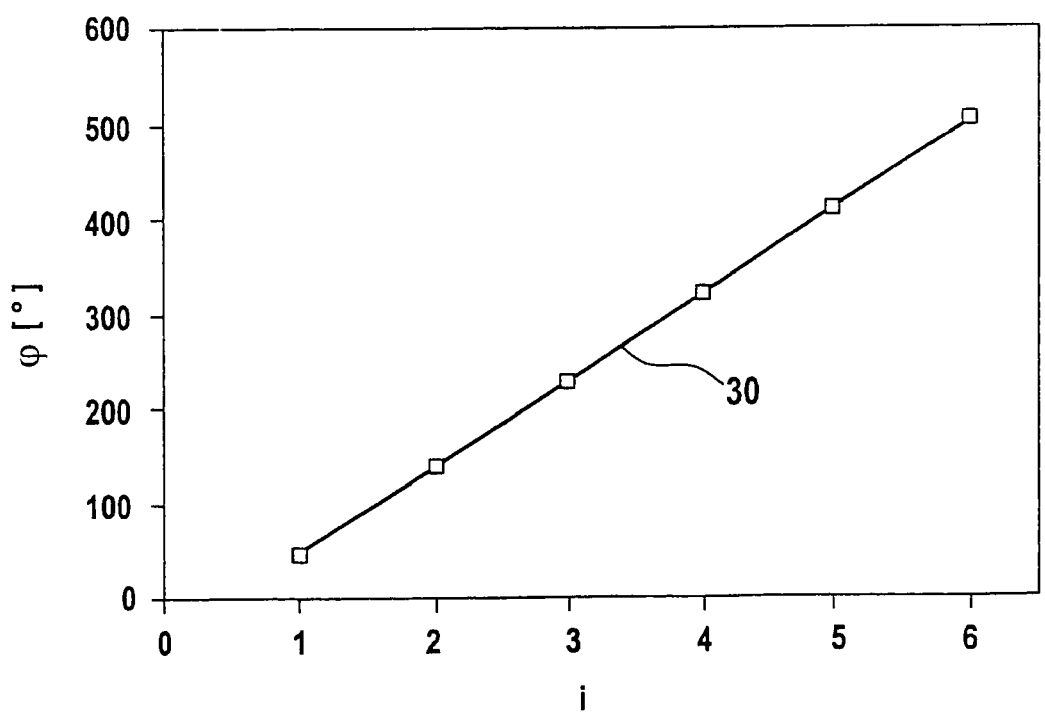
FIG. 2 shows a graph representing the phase $\phi$ of six basic images $R_i$, where i=1 . . . 6 relatively to a reference phase.

After the first basic image $R_1$ has been recorded, further basic images showing defined phase shifts are recorded, as illustrated in FIG. 2. This figure shows the phase φ, in relation to the reference phase 0°, of each of six basic images $R_i$, where i=1, . . . , 6. Any two successive basic images exhibit a phase shift Δφ of 90°. The constant phase shift produces a straight line 30 in the phase related graph.

Control of the projecting means 12 to produce the phase-shifted grid of light is likewise effected by the computer unit 16.

In one embodiment of the invention an algorithm is used which is based on the use of four basic images showing a phase shift of 90° between successive basic images. The computer unit 16 calculates, in known manner, the phase of a halftone dot from the intensities of the four basic images. In the present invention, there are recorded not four, as in the standard algorithm, but five basic images $R_1, \ldots, R_5$ which are successively out-of-phase with each other by 90°. This prolongs the recording time by 25%.

A first phase related image $P_1$ is then computed from the basic images $R_1$ to $R_4$ according to the standard algorithm and a second phase related image $P_2$ is computed from the basic images $R_2$ to $R_5$. Since the successive basic images $R_1$, $R_2$ to $R_4$, $R_5$ show a phase shift of 90° relatively to each other, the two phase related images $P_1$ and $P_2$ are also out-of-phase with each other by 90°. The two phase related images $P_1$ and $P_2$ are then averaged. Noise of 2-fold grid frequency is thus suppressed to a high degree or eliminated.

Figure 3:
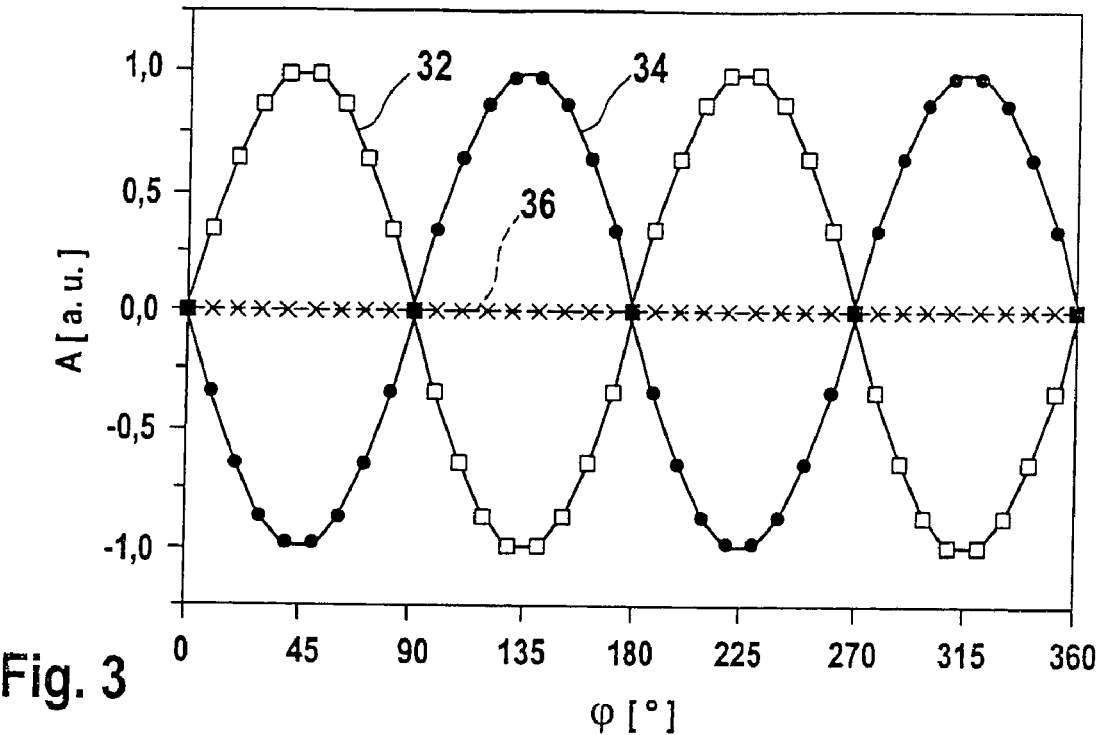
FIG. 3 shows a graph representing the amplitude A of a disturbance of 2-fold grid frequency as a function of the phase $\phi$.

This is illustrated in the graph of FIG. 3 showing the amplitude A of noise of 2-fold grid frequency as a function of the phase φ. The line 32 (light squares) shows the curve of the noise in the phase related image $P_1$, and the line 34 (bold dots) shows the curve of the noise in the phase related image $P_2$ showing a phase shift of 90°. By averaging the phase related images there is produced the curve 36 (crosses), in which the noise of 2-fold grid frequency is eliminated.

In another embodiment of the invention, the algorithm based on four basic images showing a phase shift of 90° is again used as starting point. In this embodiment, six basic images $R_1, \ldots, R_6$ successively out-of-phase by 90° are recorded. The recording time is prolonged by 50% as against the standard algorithm. Then three phase related images are computed using the standard algorithm, a first phase related image $P_1$ from the basic images $R_1$ to $R_4$, a second phase related image $P_2$ from the basic images $R_2$ to $R_5$, and a third phase related image $P_3$ from the basic images $R_3$ to $R_6$.

Figure 4:
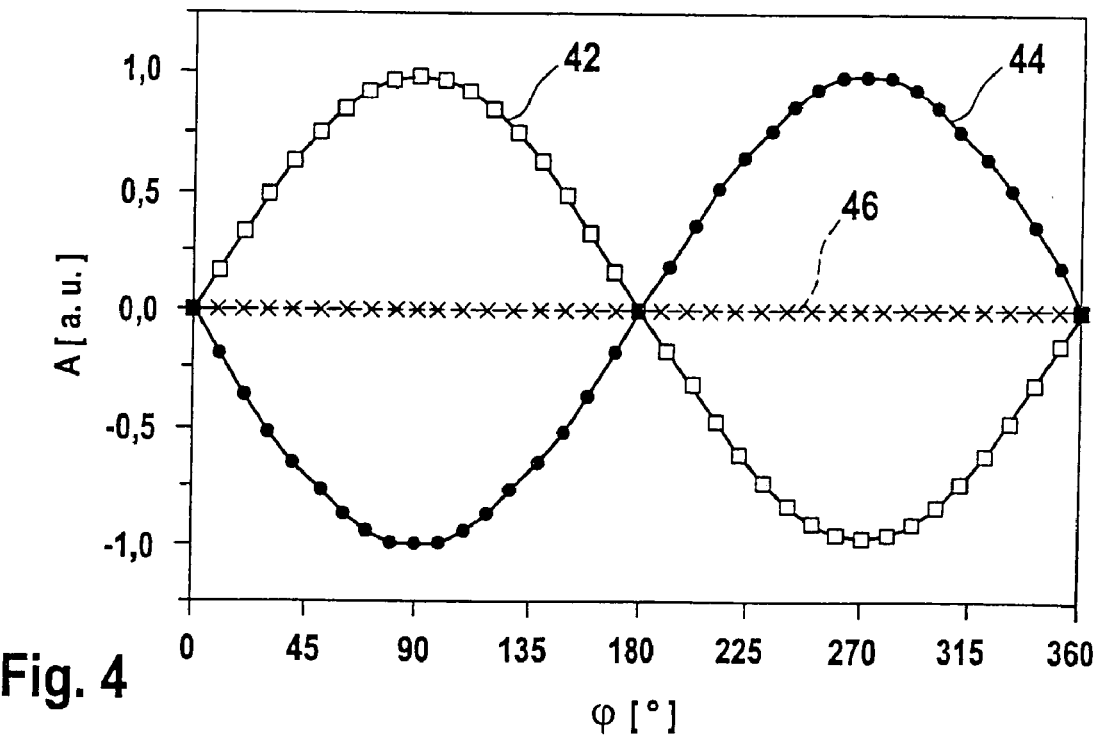
FIG. 4 shows a graph representing the amplitude A of a disturbance of 1-fold grid frequency as a function of the phase $\phi$.

Since the individual basic images of the first and third phase related images $R_1$, $R_3$ to $R_4$, $R_6$ show a phase shift of 180° relatively to each other, the two phase related images $P_1$ and $P_3$ also exhibit a phase shift of 180° relatively to each other. By averaging the phase related images $P_1$ and $P_3$, noise of 1-fold grid frequency is suppressed to a high degree or eliminated. This is illustrated in the graph of FIG. 4, which depicts the amplitude A of noise of 1-fold grid frequency as a function of the phase φ.

The line 42 (light squares) depicts the curve of the noise in the phase related image $P_1$, and the line 44 (bold dots) depicts the curve of the noise in the phase related image $P_3$ showing a phase shift of 180°. By averaging the phase related images there is produced the curve 46 (crosses), in which the noise of grid frequency is eliminated. It is then possible to average the phase related image $P_2$, as described above, with the intermediate phase related image $P_2$ obtained by averaging the phase related images $P_1$ and $P_3$, in order to eliminate noise of 2-fold grid frequency.

The statements referring to the phase related images apply equally to contrast images.

In a manner similar to that described in the above methods it is also possibly to eliminate noise of 4-fold grid frequency by averaging two phase related images or two contrast images computed from basic images showing a phase shift of 45°. During this operation a specific property of field sensors can be utilized. In the case of a phase shift of the basic images of 90° the two fields will show a phase shift of 45°. This can be utilized by averaging the two phase related images or contrast images for the elimination of noise of 4-fold grid frequency. The loss of resolution is, in the case of strong noise, more than compensated by the gain in measuring accuracy.

Periodic disturbances can occur sporadically as a response to external influences or may always be present due to the system used. For this reason, in a preferred embodiment, the occurrence of disturbances of 1-fold, 2-fold, or 4-fold grid frequency is determined by Fourier analysis of a relief image of a test object, for example, a plane.

This can be carried out without additional time expenditure during calibration of the system, as is in any case necessary. Then, depending on which multiples of the grid frequency are found, a suitable computation scheme can be used which suppresses only those disturbances having the found frequencies and can thus be carried out in as short a time as possible. The drawbacks of the aforementioned corrections, i.e., longer recording time and/or loss of resolution, do not occur unnecessarily. A longer exposure time is often particularly disadvantageous when the measuring system and the object to be imaged can be freely positioned relatively to each other.

Figure 5:
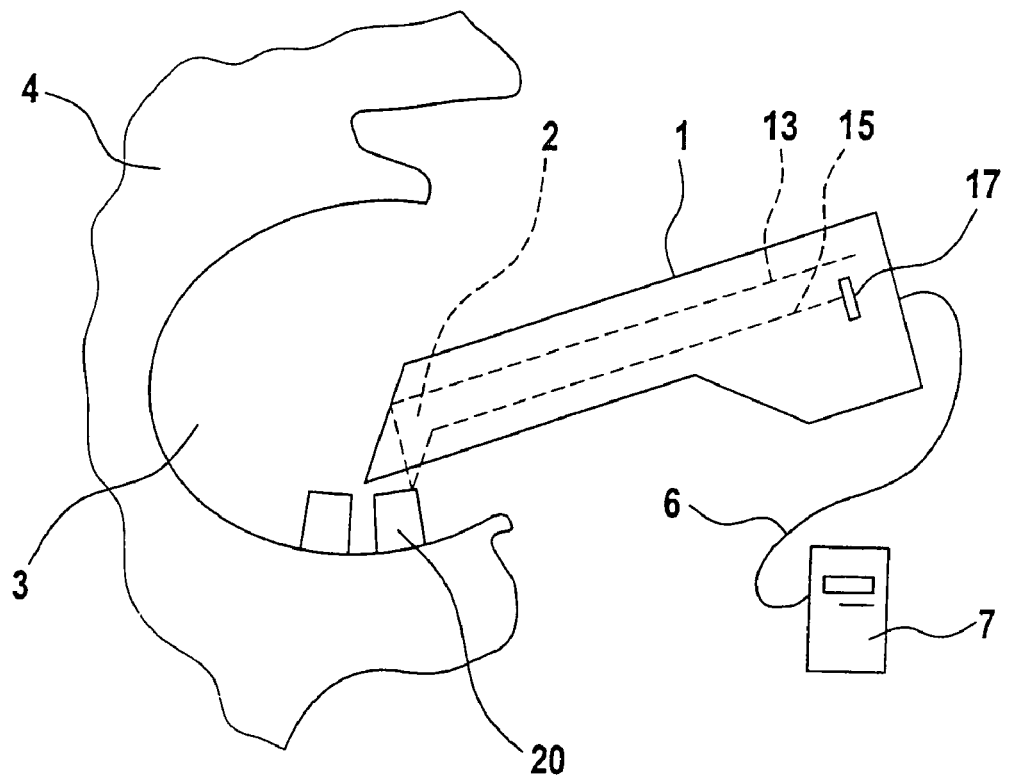
FIG. 5 is a diagrammatic drawing of an intraoral camera.

A device for carrying the described method into effect is shown in FIG. 5 in the form of an intraoral camera 1.

The intraoral camera can be introduced at one end 2 into an oral cavity 3 of a patient 4 and the recorded image data of an object 20 can be read by device 7 via a cable 6. The evaluation unit 16 computes a relief image of the object to be imaged 20 from several basic camera images that are out-of-phase with each other and are grouped so as to form at least two groups of basic images. The evaluation unit 16 can comprise components of a commercial PC. The camera 1 exhibits a projection ray trajectory 13 for the production of a striped pattern on the object to be imaged 20. Via a trajectory of observation 15 the striped pattern projected on to the object to be imaged 20 is recorded as a basic image by a detector 17.

Figure 6:
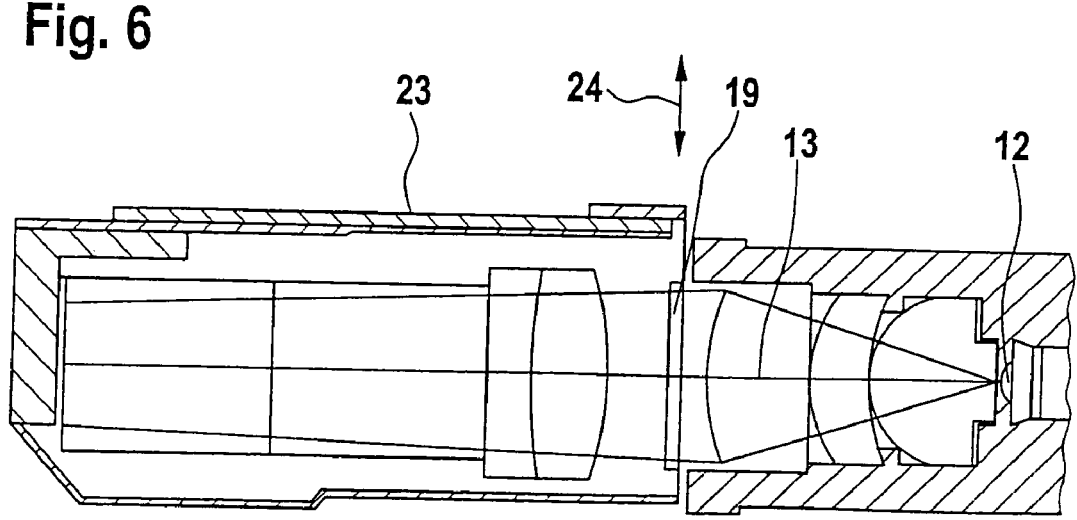
FIG. 6 is a diagrammatic representation of a portion of the projection ray trajectory of the intraoral camera of FIG. 5.

The intraoral camera of FIG. 5 contains, for this purpose, projecting means 12 illustrated in FIG. 6 for projecting a striped pattern on to the object to be imaged, said pattern being produced by a grid 19 disposed in the projection ray trajectory 13. The grid 19 is moved by a flexure-mode resonator 23 in a direction 24 substantially normal to the direction of projection. This usually takes place continuously, although the properties of the flexure-mode resonator must be taken into consideration. Since these movements are small, manufacturing variations in the behavior of the flexure-mode resonator have an influence on this movement that cannot be disregarded. Basically, it is also possible to move the grid in jumps instead of continuously such that the striped pattern stays still during the integration time, i.e. during the exposure time of the image detector.

It is to be noted that $R_m$ refers to all the basic images of the camera held in the same position. One exposure is divided in "m" shots, whereby the phase angle between the two shots has been modified. In practice, one exposition lasts about 0.5 seconds and each of the shots last about 40 ms seconds. Out of the number of "m" shots, acquired during one exposition, with the camera held in one position, an image is calculated by using the images of several shots up to a number of "n" or "m+1." Thus, the number "m" is always greater than the number "n". Depending on the method used, "m" is equal to "n+1" or "n+2".

And, the relief image may be a three-dimensional image while the contrast image may merely be a black-and-white image. The phase related image may correspond to the image of one shot.

The invention claimed is:

1. A method of imaging an object for dental purposes, comprising the steps of:
    (a) projecting using a projector a striped pattern on to the object to be imaged along an angle of projection,
    (b) recording the projected striped pattern as a basic image ($R_i$) with a picture receiver at an angle other than the angle of projection,
    (c) repeating steps (a) and (b) at a number of different positions of phase relation of the striped pattern to provide a plurality of basic images, and
    (d) computing using a computer an image of said object from the plurality of basic images that are out-of-phase with each other ($R_1 \ldots, R_n$),
wherein in order to suppress periodic disturbances,
    (d1) recording (n+2) basic images ($R_1, R_2 \ldots, R_n+2$) of which successive basic images show a phase shift,
    (d2) forming first, second and third groups of basic images ($R_1, R_2, \ldots, R_n; R_2, R_3, \ldots, R_n+1; R_3, R_4, \ldots, R_n+2$),
    (d3) computing using a computer a first phase related image ($P_1$) from the first group of basic images ($R_1, R_2, \ldots, R_n$), a second phase related image ($P_2$) from the second group of basic images ($R_2, R_3, \ldots, R_n+1$), and a third phase related image ($P_3$) from the third group of basic images ($R_3, R_4, \ldots, R_n+2$),
    (d4) averaging using a computer the first phase related image ($P_1$) and the third phase related image ($P_3$) in order to obtain an intermediate image (Pz), and averaging the second phase related image ($P_2$) and the intermediate image (Pz) in order to obtain a phase related image (P) having a reduced amount of noise, n being an integer at least equal to 3, and
    (d5) computing using a computer an image of the object to be imaged from the phase related image (P) having a reduced amount of noise.

2. The method as defined in claim 1, wherein the computed phase related images ($P_1$, $P_2$) are averaged with weighting factors.

3. The method as defined in claim 1, wherein the basic images ($R_1 \ldots, R_m$) are each recorded with a constant shift of the phase relation of the lattice (19).

4. The method as defined in claim 1, wherein n is 4.

5. The method as defined in claim 1, wherein the basic images ($R_1, \ldots, R_m$) are recorded by an interlacing method so that the two fields are out-of-phase with each other.

6. The method as defined in claim 5, wherein the two fields show a phase shift relative to each other which is equal to half the phase shift between successive basic images ($R_1, \ldots, R_m$).

7. The method as defined in claim 5, wherein a phase related image ($P_1$, $P_2$) is computed from each of the fields of a basic image ($R_1, \ldots, R_m$) and the two phase related images ($P_1$, $P_2$) are averaged prior to further processing in such a manner that a phase related image (P) having a reduced amount of high-frequency noise is formed.

8. The method as defined in claim 1, wherein prior to step a), an image of a specific test object is recorded and that on the basis of an analysis of the image of the test object a suitable scheme for use in the computation of the noise-reduced phase related image for the object to be imaged is selected.

9. The method as defined in claim 1, wherein the object to be imaged and a camera used for recording the projected striped pattern can be freely positioned relative to each other.

10. The method as defined in claim 1, wherein an image of one or more teeth in a oral cavity of a patient is recorded by manual surveying over a short measurement period.

11. The method as defined in claim 1, wherein the image to be created of said object is one of a relief image and a contrast image.

12. A device for imaging an object for dental purposes, comprising:
    projecting means for projecting a striped pattern on to the object to be imaged,
    a camera for recording the projected striped pattern in the form of basic images ($R_1, \ldots, R_m$),
    means for computing an image of the object to be imaged from a number of the basic images ($R_1, \ldots, R_m$) that are out-of-phase with each other with formation of three groups of basic images ($R_1, R_2, \ldots, R_n; R_2, R_3, \ldots, R_n+1; R_3, \ldots, R_n+2$),
    means for averaging two groups of basic images, and
    means for averaging the averaged image with a third group of images so as to obtain a phase related image having a reduced amount of noise.

13. A method of imaging an object for dental purposes, comprising the steps of:
    (a) projecting using a projector a striped pattern on to the object to be imaged,
    (b) recording the projected striped pattern as a basic image ($R_i$) with a picture receiver at an angle other than the angle of projection,
    (c) repeating steps (a) and (b) at a number of different positions of the phase relation of the striped pattern,
    (c1) wherein the basic images ($R_1, \ldots, R_m$) are recorded by an interlacing method so that the two fields are out of phase with each other, and
    (d) computing using a computer an image of said object from the plurality of basic camera images that are out-of-phase with each other ($R_1 \ldots, R_n$),
wherein in order to suppress periodic disturbances, i.e., noise, in step (d),
    (d0) wherein a phase related image ($P_1$, $P_2$) is computed using a computer from each of the fields of a basic image ($R_1, \ldots, R_m$) and the two phase related images ($P_1$, $P_2$) are averaged prior to further processing in such a manner that a phase related image (P) having a reduced amount of high-frequency noise is formed,
    (d1) forming from the basic camera ($R_1, \ldots, R_n$) images at least two groups of basic images ($R_1, R_2 \ldots, R_n; R_2$, and $R_3, \ldots, R_n+1$),
    (d2) computing using a computer a phase related image ($P_j$) of the object to be imaged from each group of basic images ($R_1, R_2, \ldots, R_n; R_2, R_3, \ldots, R_n+1$)
    (d3) averaging the computed phase related images ($P_1$, $P_2$) such that a phase related image (P) having a reduced amount of noise is formed, and
    (d4) computing using a computer an image of the object to be imaged from the phase related image (P) obtained in step (d3) having a reduced amount of noise.

14. The method as defined in claim 13, wherein the computed phase related images ($P_1$, $P_2$) are averaged with weighting factors.

15. The method as defined in claim 13, wherein the basic images ($R_1, \ldots, R_m$) are each recorded with a constant shift of the phase relation of the lattice.

16. The method as defined in claim 13, including
    recording (n+1) basic images ($R_1, R_2, \ldots, R_n+1$) successive basic images showing a phase shift,
    forming two groups of basic images ($R_1, R_2, \ldots, R_n; R_2, R_3, \ldots, R_n+1$), computing using a computer a first phase related image ($P_1$) from the first group of basic images ($R_1, R_2, \ldots, R_n$) and computing using a computer a second phase related image ($P_2$) from the second group of basic images ($R_2, R_3 \ldots, R_n+1$), and averaging the first phase related image ($P_1$) and the second phase related image ($P_2$) in order to obtain a phase related image (P) having a reduced amount of noise, n being an integer at least equal to 3.

17. The method as defined in claim 13, including
recording (n+2) basic images ($R_1, R_2 \ldots, R_n+2$) of which successive basic images show a phase shift,
forming three groups of basic images ($R_1, R_2, \ldots, R_n; R_2, R_3, \ldots, R_n+1; R_3, R_4, \ldots, R_n+2$),
computing using a computer a first phase related image ($P_1$) from the first group of basic images ($R_1, R_2, \ldots, R_n$), computing using a computer a second phase related image ($P_2$) from the second group of basic images ($R_2, R_3, \ldots, R_n+1$), and computing using a computer a third phase related image ($P_3$) from the third group of basic images ($R_3, R_4, \ldots, R_n+2$), and
averaging the first phase related image ($P_1$) and the third phase related image ($P_3$) in order to obtain an intermediate image ($P_z$), and averaging the second phase related image ($P_2$) and the intermediate image ($P_z$) in order to obtain a phase related image (P) having a reduced amount of noise, n being an integer at least equal to 3.

18. The method as defined in claim 17, wherein n is 4.

19. The method as defined in claim 13, wherein the two fields show a phase shift relative to each other which is equal to half the phase shift between successive basic images ($R_1, \ldots, R_m$).

20. The method as defined in claim 13, wherein prior to step (a), recording an image of a specific test object and on the basis of an analysis of the image of the test object selecting a suitable scheme for use in the computation of the noise-reduced phase related image for the object to be imaged.

21. The method as defined in claim 13, wherein the object to be imaged and a camera used for recording the projected striped pattern can be freely positioned relative to each other.

22. The method as defined in claim 13, wherein an image of one or more teeth in a oral cavity of a patient is recorded by manual surveying over a short measurement period.

23. The method as defined in claim 13, wherein the image to be created of said object is one of a relief image and a contrast image.

24. A device for imaging an object for dental purposes, comprising:
projecting means for projecting a striped pattern on to the object to be imaged,
a camera for recording the projected striped pattern in the form of basic images ($R_1, \ldots, R_m$),
means for computing an image of the object to be imaged from a number of the basic images ($R_1, \ldots, R_m$) that are out-of-phase with each other with formation of at least two groups of basic images ($R_1, R_2, \ldots, R_n; R_2, R_3, \ldots, R_n+1$), and
means for recording the basic images by an interlacing method so as to obtain a phase related image having a reduced amount of noise.

25. A method of imaging an object for dental purposes, comprising the steps of:
(a) projecting using a projector a striped pattern on to the object to be imaged,
(b) recording the projected striped pattern as a basic image ($R_i$) with a picture receiver at an angle other than the angle of projection,
steps (a) and (b) being carried out at a number of different positions of the phase relation of the striped pattern to provide a plurality of basic images, and
(c) computing using a computer an image of said object from the plurality of basic images that are out-of-phase with each other ($R_1, \ldots, R_n$),
wherein in order to suppress periodic noise disturbances in step (c),
(c1) forming from the basic camera ($R_1, \ldots, R_m$) images at least two groups of basic images ($R_1, R_2, \ldots, R_n; R_2,$ and $R_3, \ldots, R_n+1$),
(c2) computing using a computer a contrast image ($P_j$) of the object to be imaged from each group of basic images ($R_1, R_2, \ldots, R_n; R_2, R_3, \ldots, R_n+1$)
(c3) averaging the computed contrast images ($P_1, P_2$) such that a contrast image (P) having a reduced amount of noise is formed, and
(c4) computing using a computer an image of the object to be imaged from the contrast image (P) having a reduced amount of noise.

26. The method as defined in claim 25, wherein the computed contrast images ($P_1, P_2$) are averaged with weighting factors.

27. The method as defined in claim 25, wherein the basic images ($R_1, \ldots, R_m$) are each recorded with a constant shift of the phase relation of the lattice (19).

28. The method as defined in claim 25, wherein
recording (n+1) basic images ($R_1, R_2, \ldots, R_n+1$) successive basic images showing a phase shift,
forming two groups of basic images ($R_1, R_2, \ldots, R_n; R_2, R_3, \ldots, R_n+1$),
computing using a computer a first contrast image ($P_1$) from the first group of basic images ($R_1, R_2, \ldots, R_n$) and computing using a computer a second contrast image ($P_2$) from the second group of basic images ($R_2, R_3 \ldots, R_n+1$), and
averaging the first contrast image ($P_1$) and the second contrast image ($P_2$) in order to obtain a contrast image (P) having a reduced amount of noise, n being an integer at least equal to 3.

29. The method as defined in claim 25, including
recording (n+2) basic images ($R_1, R_2 \ldots, R_n+2$) of which successive basic images show a phase shift,
forming three groups of basic images ($R_1, R_2, \ldots, R_n; R_2, R_3, \ldots, R_n+1; R_3, R_4, \ldots, R_n+2$),
computing using a computer a first contrast image ($P_1$) from the first group of basic images ($R_1, R_2, \ldots, R_n$), computing using a computer a second contrast image (P2) from the second group of basic images ($R_2, R_3, \ldots, R_n+1$), and computing using a computer a third contrast image ($P_3$) from the third group of basic images ($R_3, R_4, \ldots, R_n+2$), and
averaging the first contrast image ($P_1$) and the third contrast image ($P_3$) in order to obtain an intermediate image (Pz), and averaging the second contrast image ($P_2$) and the intermediate image (Pz) in order to obtain a contrast image (P) having a reduced amount of noise, n being an integer at least equal to 3.

30. The method as defined in claim 29, wherein n is 4.

31. The method as defined in claim 25, including recording the basic images ($R_1, \ldots, R_m$) by an interlacing method so that the two fields are out-of-phase with each other.

32. The method as defined in claim 31, wherein the two fields show a phase shift relative to each other which is equal to half the phase shift between successive basic images ($R_1, \ldots, R_m$).

33. The method as defined in claim 31, wherein a contrast image ($P_1$, $P_2$) is computed using a computer from each of the fields of a basic image ($R_1, \ldots, R_m$) and the two contrast images ($P_1$, $P_2$) are averaged prior to further processing in such a manner that a contrast image (P) having a reduced amount of high-frequency noise is formed.

34. The method as defined in claim 25, wherein prior to step a), recording an image of a specific test object and on the basis of an analysis of the image of the test object selecting a suitable scheme for use in the computation of the noise-reduced contrast image for the object to be imaged.

35. The method as defined in claim 25, wherein the object to be imaged and a camera used for recording the projected striped pattern can be freely positioned relative to each other.

36. The method as defined in claim 25, wherein an image of one or more teeth in a oral cavity of a patient is recorded by manual surveying over a short measurement period.

37. A device for imaging an object for dental purposes, comprising projecting means for projecting a striped pattern on to the object to be imaged, a camera for recording the projected striped pattern in the form of basic images ($R_1, \ldots, R_m$), means for computing an image of the object to be imaged from a number of the basic images ($R_1, \ldots, R_m$) that are out-of-phase with each other with formation of at least two groups of basic images ($R_1, R_2, \ldots, R_n$; $R_2, R_3, \ldots, R_n+1$), and means for computing a contrast image from the at least two groups of basic images so as to obtain a phase shifted image having a reduced amount of noise.

\* \* \* \* \*